United States Patent
Jeffery et al.

(10) Patent No.: US 10,936,277 B2
(45) Date of Patent: Mar. 2, 2021

(54) CALIBRATION METHOD FOR CUSTOMIZABLE PERSONAL SOUND DELIVERY SYSTEM

(71) Applicant: Audeara Pty Ltd.

(72) Inventors: Christopher Arnold Jeffery, Red Hill (AU); James Alexander Fielding, Red Hill (AU); Alex John Afflick, Red Hill (AU)

(73) Assignee: Audeara Pty Ltd., St. Lucia (AU)

( * ) Notice: Subject to any disclaimer, the term of this patent is extended or adjusted under 35 U.S.C. 154(b) by 9 days.

(21) Appl. No.: 16/043,351

(22) Filed: Jul. 24, 2018

(65) Prior Publication Data

US 2018/0364971 A1 Dec. 20, 2018

Related U.S. Application Data

(63) Continuation-in-part of application No. 15/196,256, filed on Jun. 29, 2016, now abandoned.

(30) Foreign Application Priority Data

Jun. 29, 2015 (AU) .............................. 2015902532

(51) Int. Cl.
*G06F 3/16* (2006.01)
*A61B 5/12* (2006.01)
(Continued)

(52) U.S. Cl.
CPC .............. *G06F 3/165* (2013.01); *A61B 5/123* (2013.01); *A61B 5/6898* (2013.01);
(Continued)

(58) Field of Classification Search
CPC ....... G06F 3/165; A61B 5/123; A61B 5/6898; A61B 5/7282; A61B 5/7475
(Continued)

(56) References Cited

U.S. PATENT DOCUMENTS 6,668,204 B2 12/2003 Neoh
8,059,833 B2 11/2011 Koh
(Continued)

FOREIGN PATENT DOCUMENTS

| AU | 2016100861 | 7/2016 |
| TW | 1629906 | 7/2018 |
| WO | 2015124598 | 8/2015 |

OTHER PUBLICATIONS

ISR from PCT/AU2019/050764.

*Primary Examiner* — Yosef K Laekemariam
(74) *Attorney, Agent, or Firm* — Stephen T. Scherrer; Monique A. Morneault; Scherrer Patent & Trademark Law, P.C.

(57) ABSTRACT

A method (100) for calibrating a sound delivery system (1) having a processing assembly, a data communications assembly (9) coupled to the processing assembly, and at least one audio transducer (21a, 21b) mounted with at least one processor (11) of the processing assembly and responsive thereto for delivering sound to a user (3), the method including the steps of: transmitting from a remote user interface device (6) for the sound delivery system, a sequence of command codes for specifying predetermined characteristics of test sounds; receiving the command code sequence at the communications assembly of the sound delivery system; providing the command code sequence to the processing assembly of the sound delivery system; reproducing by a selected at least one audio transducer, the predetermined test sounds under control of said at least one processor according to the command code sequence; measuring with a reference SPL meter (70) proximate to the audio transducer, characteristics of test sounds reproduced by the sound delivery system; comparing the measured characteristics of the reproduced sounds with the predetermined characteristics of the test sounds; producing a map- (Continued)

ping of specified test sounds to sounds reproduced by said at least one audio transducer; and storing the mapping in an electronic memory (12, 82) associated with the processing assembly or remote interface device (6).

14 Claims, 19 Drawing Sheets

(51) Int. Cl.
    *A61B 5/00* (2006.01)
    *H04R 5/04* (2006.01)
    *H04R 5/033* (2006.01)
    *H04R 3/04* (2006.01)
    *H04R 25/00* (2006.01)

(52) U.S. Cl.
    CPC .......... *A61B 5/7475* (2013.01); *H04R 5/04* (2013.01); *A61B 5/002* (2013.01); *A61B 5/486* (2013.01); *A61B 2505/09* (2013.01); *H04R 3/04* (2013.01); *H04R 5/033* (2013.01); *H04R 25/70* (2013.01); *H04R 2205/041* (2013.01); *H04R 2420/07* (2013.01)

(58) Field of Classification Search
    USPC ............... 381/60, 74, 309, 328, 370, 380
    See application file for complete search history.

(56) References Cited

U.S. PATENT DOCUMENTS

| | | | |
|---|---|---|---|
| 8,060,149 | B1 | 11/2011 | Louis |
| 9,319,830 | B2 | 4/2016 | Sawai |
| 10,057,674 | B1 | 8/2018 | Tseng et al. |
| 2004/0131206 | A1 | 7/2004 | Cao |
| 2005/0078838 | A1 | 4/2005 | Simon |
| 2007/0110256 | A1 | 5/2007 | Slevin |
| 2011/0009770 | A1 | 1/2011 | Margolis et al. |
| 2011/0280409 | A1 | 11/2011 | Michael |
| 2012/0239391 | A1 | 9/2012 | Duwenhorst |
| 2013/0223661 | A1 | 8/2013 | Uzuanis |
| 2013/0236023 | A1* | 9/2013 | Horbach ............ H04R 29/00 381/59 |
| 2013/0345594 | A1* | 12/2013 | Ganter ............ A61B 5/123 600/559 |
| 2014/0086434 | A1 | 3/2014 | Bang |
| 2014/0309549 | A1 | 10/2014 | Selig |
| 2014/0314261 | A1 | 10/2014 | Selig et al. |
| 2016/0020744 | A1* | 1/2016 | Kok ............ H04R 25/70 381/57 |
| 2016/0277855 | A1 | 9/2016 | Raz |
| 2017/0070818 | A1 | 3/2017 | Bang |

* cited by examiner

HEADPHONES

BONE CONDUCTION

| LEFT TRANSDUCER (21a) | | | |
|---|---|---|---|
| Frequency | Requested SPL (dB A) | Measured SPL (dB A) | SPL Offset |
| 250 Hz | 0 | 0 | 0 |
| | 10 | 9 | -1 |
| | 20 | 18 | -2 |
| | 30 | 27 | -3 |
| | 40 | 36 | -4 |
| | 50 | 45 | -5 |
| | 60 | 57 | -4 |
| | 70 | 67 | -3 |
| | 80 | 78 | -2 |
| | 90 | 89 | -1 |
| | 100 | 90 | 0 |
| | 110 | 112 | +2 |
| | 120 | 123 | +3 |
| 500Hz | 0 | 0 | 0 |
| | 10 | 10 | 0 |
| | 20 | 19 | -1 |
| | 30 | 28 | -2 |
| | 40 | 37 | -3 |
| | 50 | 46 | -4 |
| | 60 | 56 | -4 |
| | 70 | 67 | -3 |
| | 80 | 78 | -2 |
| | 90 | 89 | -1 |
| | 100 | 90 | 0 |
| | 110 | 112 | +1 |
| | 120 | 123 | +2 |
| 1kHz | 0 | 0 | 0 |
| | 10 | 10 | 0 |
| | | | |
| | | | |
| | | | |
| | | | |
| | | | |
| | | | |
| | | | |
| | | | |
| | | | |
| | | | |

Calibration Test Results Table

FIG. 17

CALIBRATION METHOD FOR CUSTOMIZABLE PERSONAL SOUND DELIVERY SYSTEM

RELATED APPLICATIONS

The present application is a continuation-in-part of U.S. patent application Ser. No. 15/196,256 filed 29 Jun. 2016 in the name of the present applicant and published as No. US 2017/0046120 A1 on 16 Feb. 2017, and incorporated herein by reference.

TECHNICAL FIELD

The present invention relates to a calibration method for sound delivery systems of the kind which involve audio transducers such as headphones, ear plugs or in some circumstances bone conduction transducers and which can be customized by a user to take into account the user's auditory response, and to sound delivery systems subject to the calibration method of the invention.

BACKGROUND

Any references to methods, apparatus or documents of the prior art are not to be taken as constituting any evidence or admission that they formed, or form part of the common general knowledge in Australia or any other country.

Different people have different auditory responses. For example, younger people are typically able to hear audio frequencies at higher frequencies than older people. As people age, or as a result of hearing damage due to exposure to loud sounds, their hearing tends to deteriorate and their auditory response across a range of frequencies changes.

It is known to provide programmable hearing aids that can, through testing of the user by an audiologist, be set to compensate for the user's deteriorated hearing acuity or partial hearing loss. However, such systems require that the user makes an appointment to have a hearing aid test, typically employing expensive and cumbersome test equipment, and that the hearing aid be set by the technician.

It has been further realized that in order to provide effective compensation for hearing loss, it is important that the audio transducers provided in a hearing compensation system be accurately calibrated during manufacture and/or assembly so that the tests undertaken by the user provide consistent and reliable performance, including irrespective of a user-supplied interface device.

It is an object of the present invention to provide a method for calibrating a sound delivery system utilized for automatic hearing tests. It is a further object of the invention to provide a customizable personal sound delivery system that is pre-calibrated using the method for convenient use and which can automatically test the user's hearing and subsequently make adjustments to its sound delivery parameters on the basis of the test results.

SUMMARY OF THE INVENTION

According to a first aspect of the present invention there is provided a method for calibrating a sound delivery system having a processing assembly, a data communications assembly coupled to the processing assembly, and at least one audio transducer mounted with at least one processor of the processing assembly and responsive thereto for delivering sound to a user, the method including the steps of:

transmitting from a remote user interface device for the sound delivery system, a sequence of command codes for specifying predetermined characteristics of test sounds;

receiving the command code sequence at the communications assembly of the sound delivery system;

providing the command code sequence to said processing assembly of the sound delivery system;

reproducing by a selected at least one audio transducer, the predetermined test sounds under control of said at least one processor according to the command code sequence;

measuring with a reference meter proximate to the audio transducer, characteristics of test sounds reproduced by the sound delivery system;

comparing the measured characteristics of the reproduced sounds with the predetermined characteristics of the test sounds;

producing a mapping of specified test sounds to sounds reproduced by said at least one audio transducer; and storing the mapping in an electronic memory associated with the remote user interface.

Preferably, the transmitting step involves use of wireless transmission employing a local or near field communications standard, such as Wi-Fi or Bluetooth.

The user interface device suitably comprises a portable computational device, such as a smartwatch, smartphone, tablet or laptop computer.

In preference, the test sounds or tones include a sequence of discrete sounds of different frequencies and sound pressure levels (SPL) within each frequency, suitably covering a typical range of human hearing.

Preferably, the test sounds are in the range of frequencies from 10 Hz to 30 kHz, suitably 20 Hz to 20 kHz, most preferably including 100 Hz, 250 Hz, 500 Hz, 1 kHz, 2 kHz, 4 KHz, 8 kHz and 16 kHz, and of sound pressure level (SPL) ranging from −10 dB to 120 dB, suitably 0 dB to 110 dB, within each discrete sound frequency.

Each of the discrete sounds in the sequence is desirably of equal duration and suitably spaced apart from adjacent sounds by periods of silence. Suitably the sound duration is in a range from 0.1 milliseconds to 5 seconds, suitably 100 milliseconds to 1 second and the intervening silence period is in a range from 0.1 milliseconds to 5 seconds, suitably 100 milliseconds to 1 second.

Suitably the storing step involves storing the test sound mapping in a code base utilized by an audio application interface of the sound delivery system. Desirably, the sound delivery system includes a non-volatile electronic memory arranged to store the code base. Most preferably, the code base is stored remotely in a database and associated with an interface application for the sound delivery system, for down-loading with the interface application on request.

The sound delivery system may be an audiological testing apparatus, such as a hearing aid, set of headphones, or other head-mountable hearing apparatus incorporating an audio transducer.

In another form, there is also provided a sound delivery system including: a processing assembly including at least one processor and an electronic memory; a user interface coupled to the at least one processing assembly; at least one audio transducer responsive to the processing assembly for delivering sound to a user; and the electronic memory accessible by the at least one processor and storing: instructions for the processor to determine compensatory weights at each of a number of audio frequencies for the user on the basis of user responses via the interface to sounds delivered via the audio transducer and to deliver audio signals to the user modified in accordance with the determined weights via said audio transducer; a code base utilised by an audio application interface of the sound delivery system; wherein the sounds delivered via the transducer for determining the compensatory weights are generated by a transducer processor mounted within a transducer portion which includes the at least one audio transducer; and wherein the sound delivery system is calibrated in accordance with the method set out above.

Preferably, the processing assembly is mounted with the at least one audio transducer; suitably in the form of a set of headphones including a pair of speakers.

In a second aspect of the invention, there is provided a sound delivery system including: at least one processing assembly; an interface coupled to the at least one processing assembly; and at least one audio transducer responsive to the at least one processing assembly for delivering sound to a user; wherein the at least one processing assembly is arranged to determine compensatory weights at each of a number of audio frequencies for the user on the basis of user responses via the interface to sounds delivered via the audio transducer and to deliver audio signals to the user modified in accordance with the determined weights via said audio transducer.

In a preferred embodiment of the invention the sound delivery system comprises an interface portion which includes the user interface and a transducer portion which includes the at least one audio transducer, wherein the first interface portion and the transducer portion include corresponding data communication assemblies for data communication there between.

Preferably the at least one processing assembly includes: at least one interface processor that is mounted within the interface portion and coupled to the user interface; and at least one transducer processor that is mounted within the transducer portion and arranged to process sound signals for delivery as sound by said audio transducer.

Preferably the data communication assemblies are arranged for wireless data communication. For example the data communication assemblies may be arranged to implement data communication according to the Bluetooth standard.

In a preferred embodiment of the invention the interface portion comprises a smartphone though it could alternatively be a tablet, laptop or desktop computer, for example.

According to another aspect of the present invention there is provided a sound delivery system including: at least one processing assembly; an interface coupled to the at least one processing assembly; at least one audio transducer responsive to the at least one processing assembly for delivering sound to a user; and an electronic memory accessible by the at least one processing assembly storing: instructions for the processor to determine compensatory weights at each of a number of audio frequencies for the user on the basis of user responses via the interface to sounds delivered via the audio transducer and to deliver audio signals to the user modified in accordance with the determined weights via said audio transducer.

In a further aspect of the invention there is provided an automatic audiological testing apparatus including: a processing assembly having at least one processor; an electronic memory in communication with the processing assembly and containing instructions for execution by said at least one processor; a user interface in communication with the processing assembly; and at least one audio transducer mounted with the processing assembly and responsive to the at least one processor for delivering sound to a user; wherein the electronic memory stores instructions for the processor to determine compensatory weights at each of a number of audio frequencies for the user on the basis of user responses via the interface to sounds at a number of different frequencies wherein the sounds delivered via the transducer for determining the compensatory weights are generated by a transducer processor mounted within a transducer portion which includes the at least one audio transducer; and wherein the audiological testing apparatus is calibrated in accordance with the method set out above.

According to a still further aspect of the present invention there is provided a set of headphones including right and left loudspeakers for delivery of sounds to a user: at least one processor configured to receive gain adjustment weights for the user for each of a number of predetermined frequencies; wherein the processor is arranged to convert an audio signal into the frequency domain, apply the gain adjustment weights to the audio signal in the frequency domain and convert the adjusted audio signal back into the time domain for delivery of an adjusted audio signal to the user via the loudspeakers.

According to another aspect of the present invention there is provided a method for sound delivery to a user including: presenting sounds of different frequencies and prompts to a user in order to determine an audiological model of the user comprising a set of gain adjustment weights for each of the different frequencies; and adjusting audio signals according to the adjustment weights to thereby deliver adjusted audio signals to the user to compensate for hearing deficiencies of the user.

Preferably the method includes facilitating adjustment of the weights by the user to introduce frequency equalization parameters selected by the user for each of a number of frequency bands.

It will therefore be realized that in one embodiment of the invention there is provided a sound delivery system that includes a processing assembly with a user interface coupled thereto. At least one audio transducer is provided for delivering sound to a user, which is responsive to the processing assembly. Typically the audio transducer is a loudspeaker of a pair of headphones or earbuds, though it may also be a bone conduction transducer. The at least one processing assembly is arranged to determine compensatory weights at each of a number of audio frequencies for the user on the basis of user responses via the interface to sounds delivered via the audio transducer and to deliver audio signals to the user modified in accordance with the determined weights via the audio transducer.

Additional features and advantages of the present invention are described in, and will be apparent from, the detailed description of the presently preferred embodiments and from the drawings.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows:

FIG. 17 is a table illustrating an example of results obtained from the calibration method of the embodiment.

DETAILED DESCRIPTION OF PREFERRED EMBODIMENTS

Figure 1:
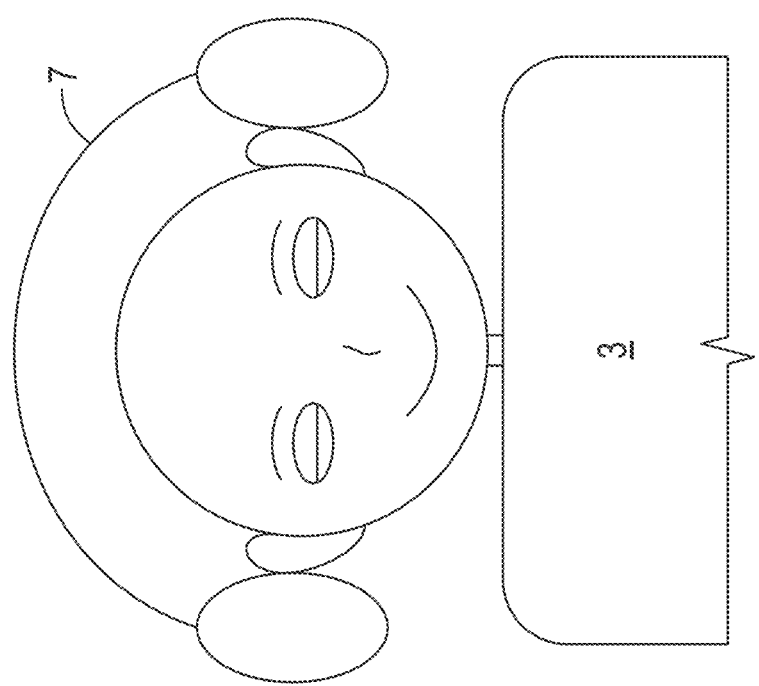
FIG. 1 is a high level diagram of a sound delivery system according to a preferred embodiment of a first aspect of the present invention, in use.
Figure 1:
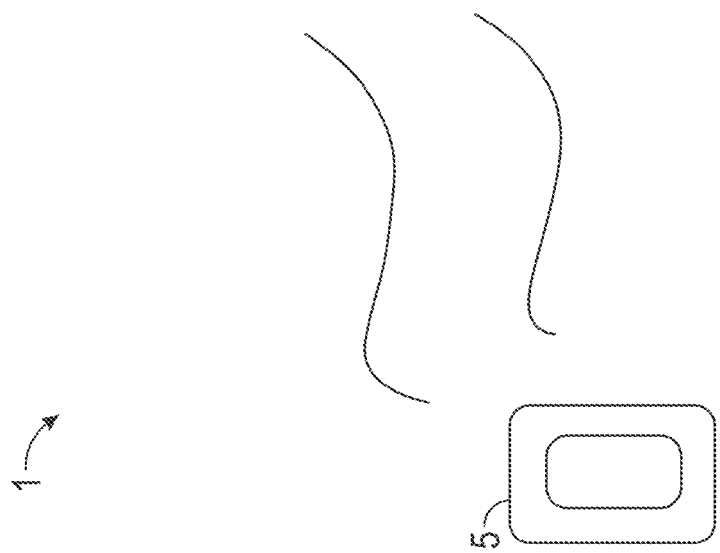

Referring now to FIG. 1, there is depicted a sound delivery system 1 in use and being applied to a user 3. In the presently described preferred embodiment the sound delivery system 1 is comprised of two major portions. A first portion comprises a smartphone 5, or other computational device such as a laptop, desktop or tablet computer. The smartphone 5 is in data communication with a second portion of the sound delivery system being a transducer portion, which in the present embodiment comprises headphones 7 though it might equally be a set of earbuds or some other sound delivery apparatus. The data communication between the smartphone 5 and the headphones 7 is by Bluetooth wireless in the presently described embodiment though of course it could be established otherwise, for example through a wired connection or by other wireless protocols.

Figure 2:
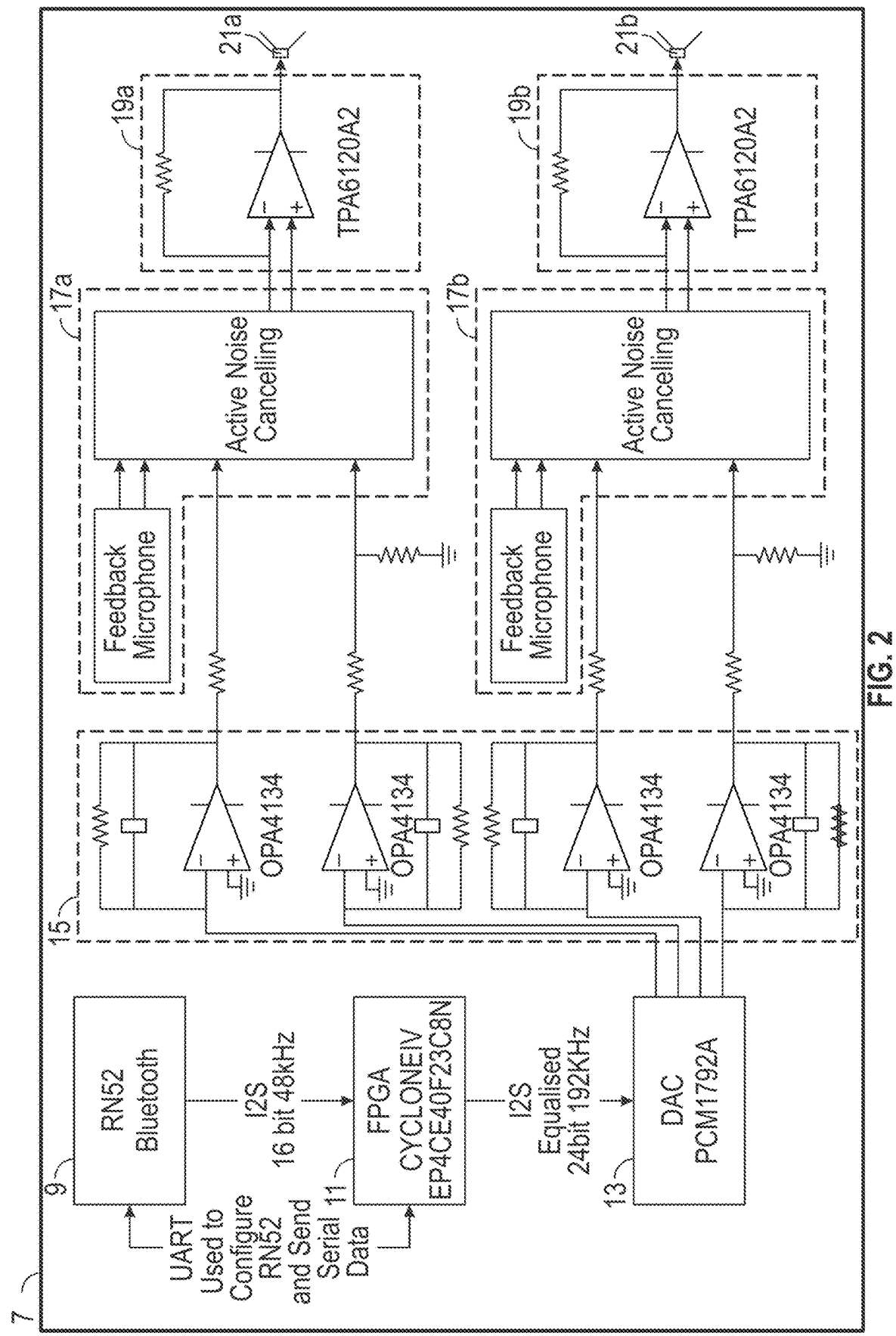
FIG. 2 is a block diagram of electronic circuitry of a transducer portion of the sound delivery system.
Figure 3A:
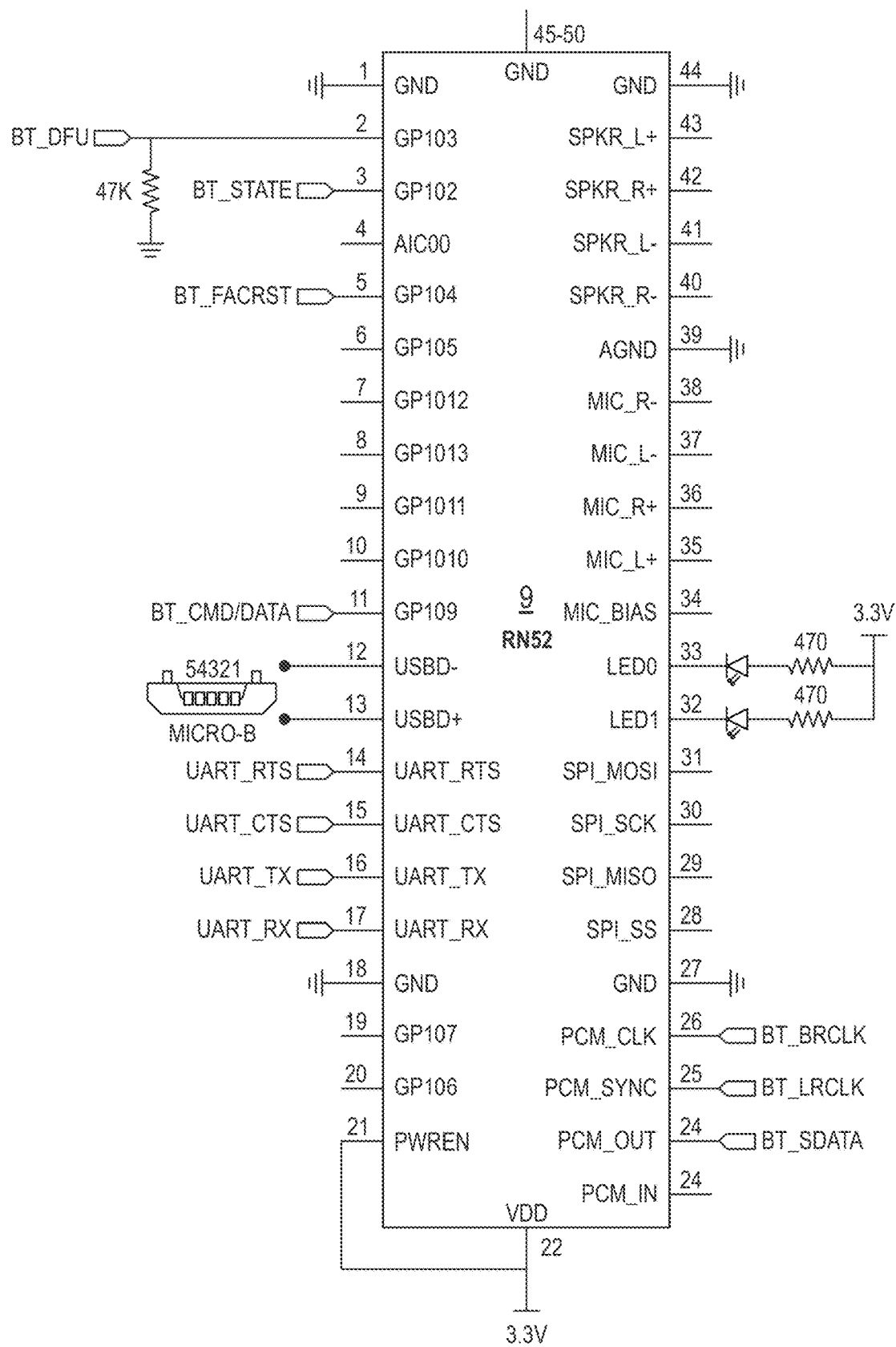
FIGS. 3A-3D are a first portion of a circuit schematic generally corresponding to the block diagram of FIG. 2.
Figure 3B:
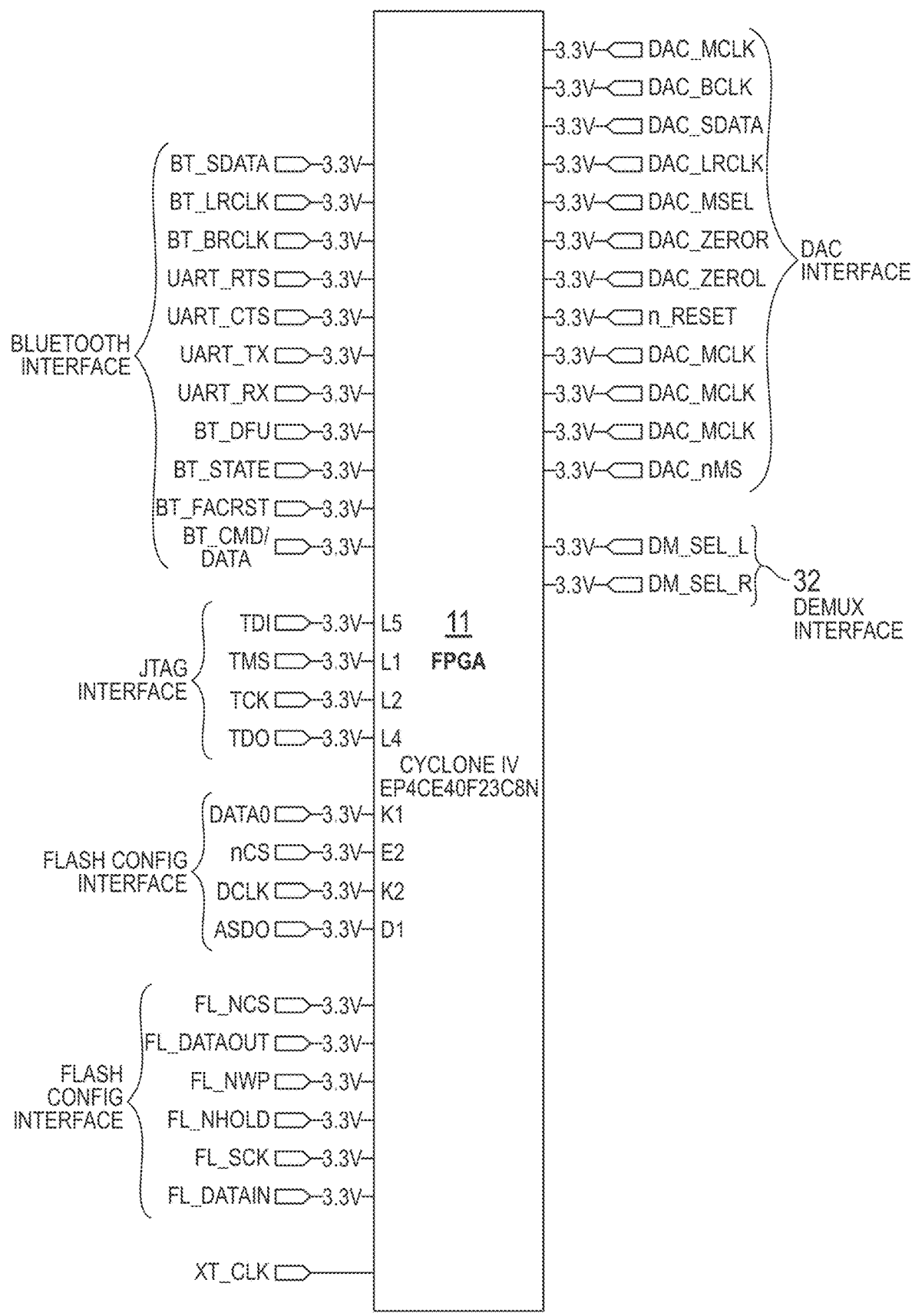
Figure 3C:
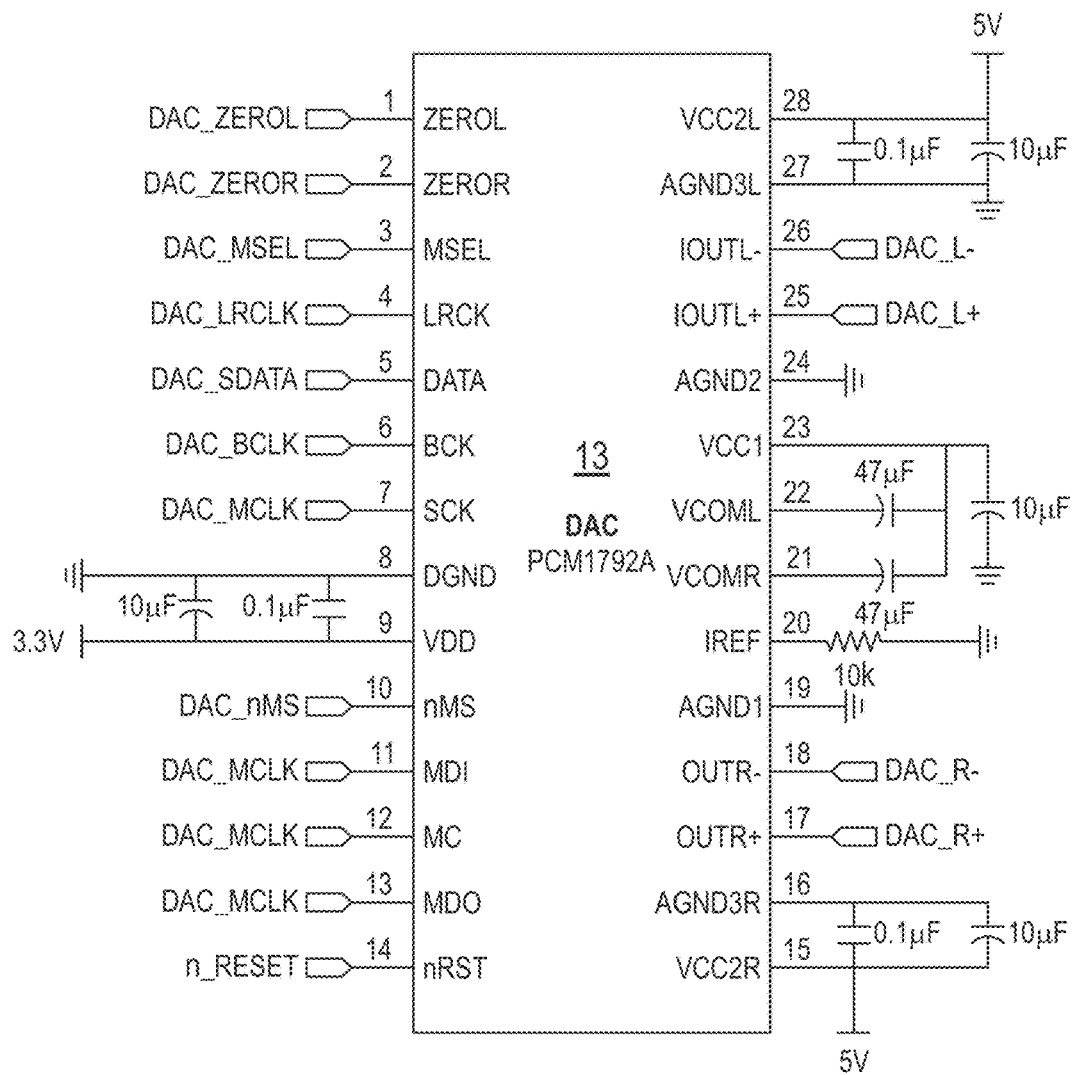
Figure 3C:
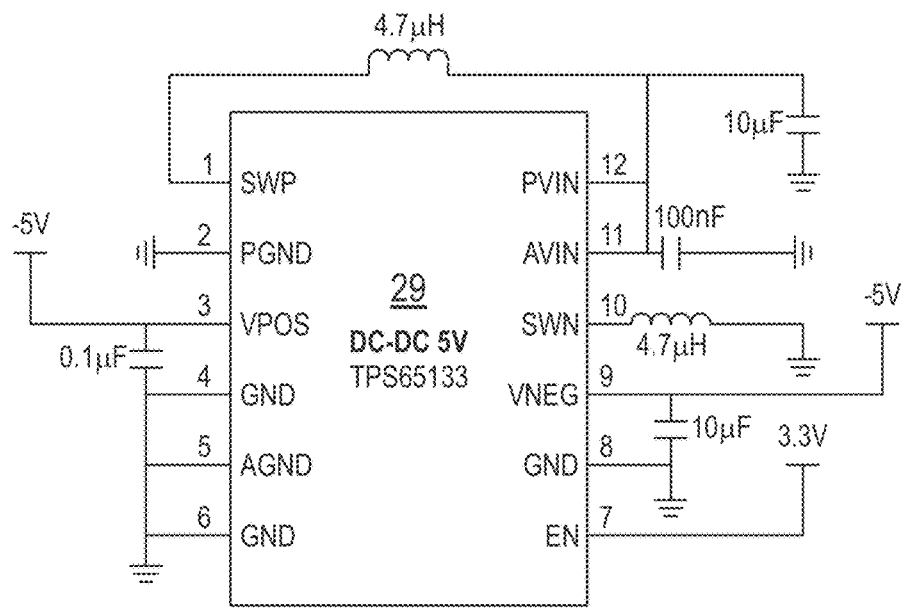
Figure 3D:
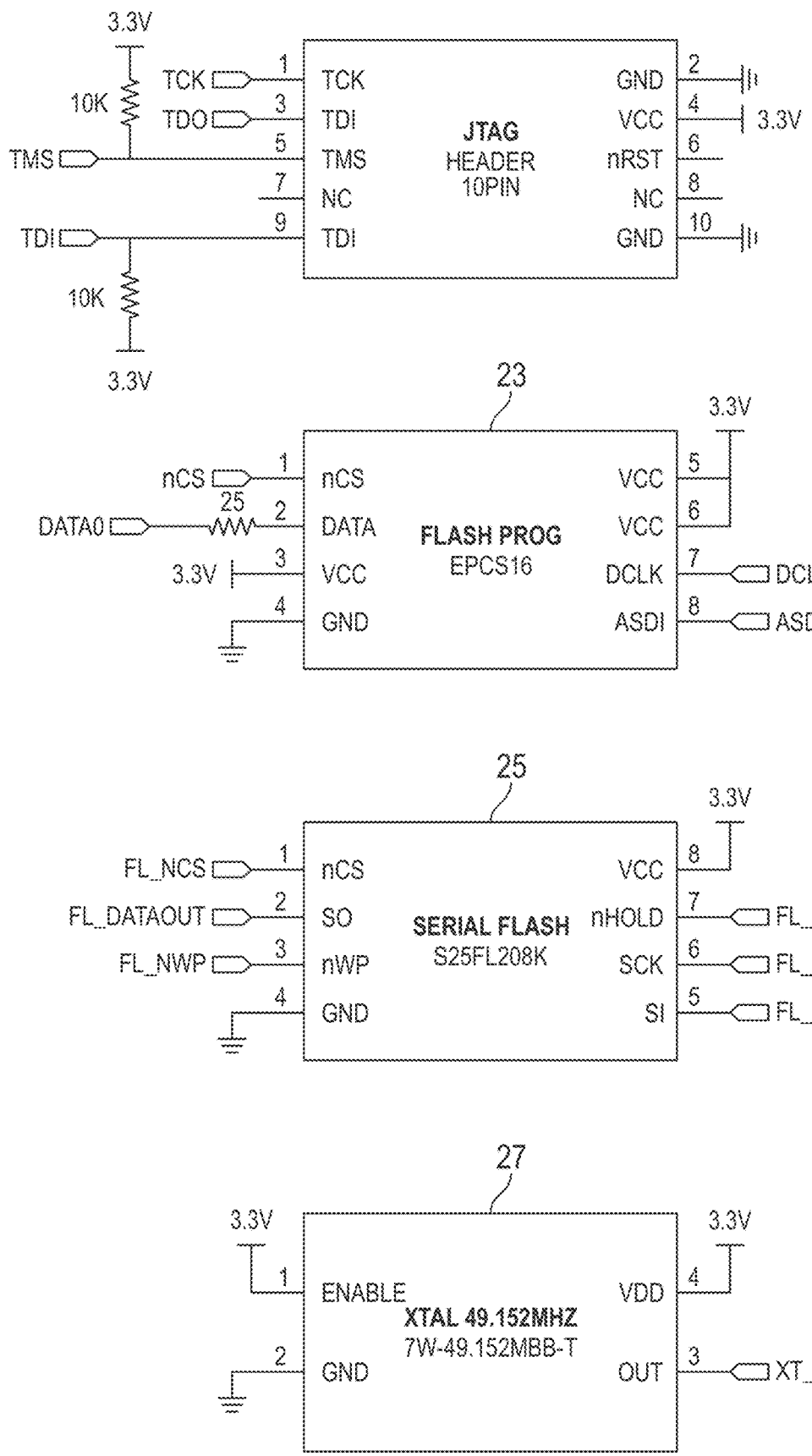

FIG. 2 is a high level block diagram of the electronic circuitry that is contained within the headphones 7. The circuitry includes a communications port 9 in the form of a Bluetooth port for communicating with the smartphone 5. A processor in the form of a field programmable gate array 11 is coupled to the Bluetooth port 8. As will be explained, the FPGA 11 is configured by uploading data from the smartphone 5 to apply "weights", i.e. gain adjustment parameters, for different frequencies to an audio signal that it receives from smartphone. An output side of the FPGA 11 is coupled to a digital to analogue converter (DAC) 13. The DAC converts the digital audio signal from the FPGA into right and left stereo analogue signals which are applied via pre-amplifiers 15a, 15b, through noise cancelling modules 17a, 17b to output amplifiers 19a, 19b. The output amplifiers 19a, 19b drive electric signal to vibration transducers 21a, 21b. The transducers 21a, 21b are typically loudspeakers though they could alternatively be bone conduction transducers.

FIGS. 3A-3D are a first part of a circuit schematic corresponding to block diagram 3 and showing the Bluetooth port 9, FPGA 11 and DAC 13. FIGS. 3A-3D also shows programmable flash components 23 and 25 which are used to configure the FPGA, for example to set the frequency gain adjustments weights that the FPGA will apply to an audio signal in use. The FPGA 11 is a Cyclone IV EP4CE40F integrated circuit that is manufactured by Altera Corporation and which is configured to perform Fast Fourier Transforms on audio signals received via the Bluetooth port, apply the gain weights in the frequency domain and then perform an Inverse Fast Fourier Transform to convert the digital signal back to the time domain.

FIGS. 3A-3D also shows a clock module 27 and a power supply chip 29 for applying power to the various components. All of these components are readily available commercially.

Figure 4A:
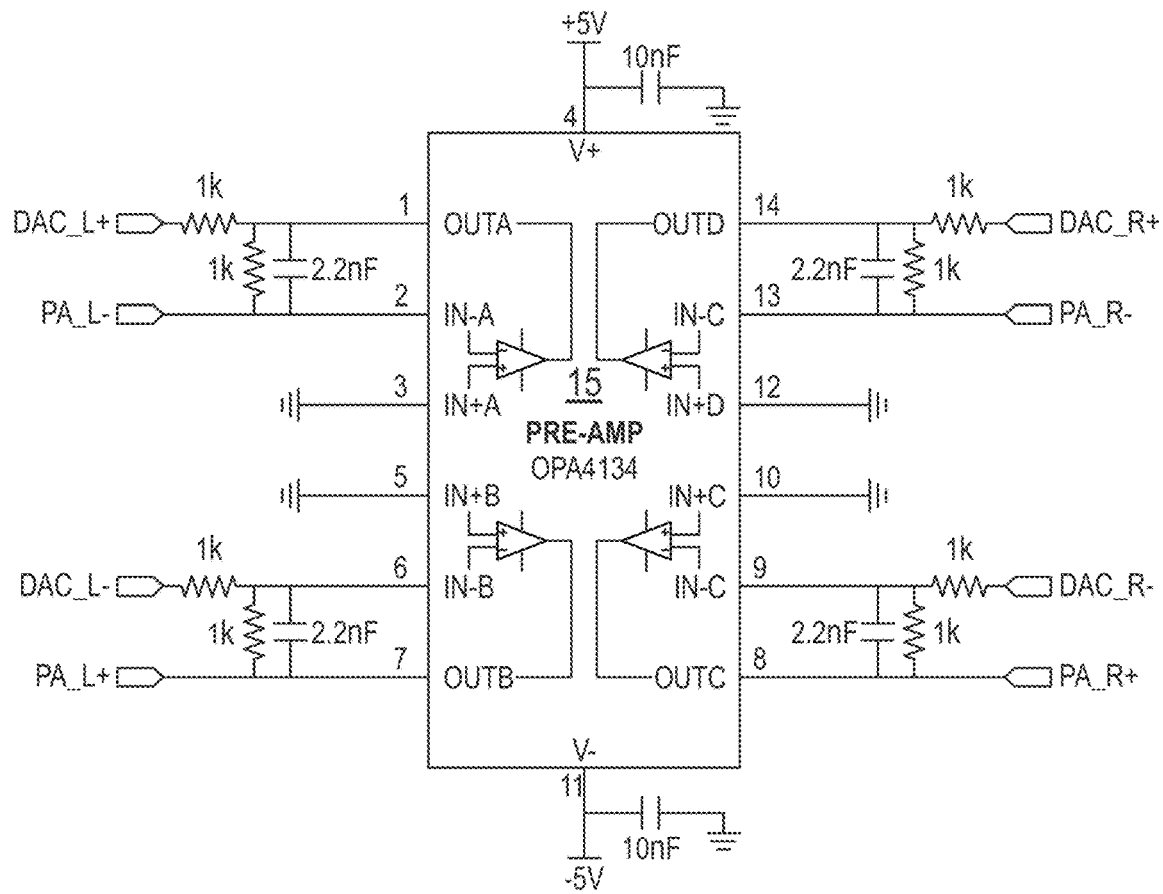
FIGS. 4A-4B are a second portion of the circuit schematic of FIG. 3.
Figure 4A:
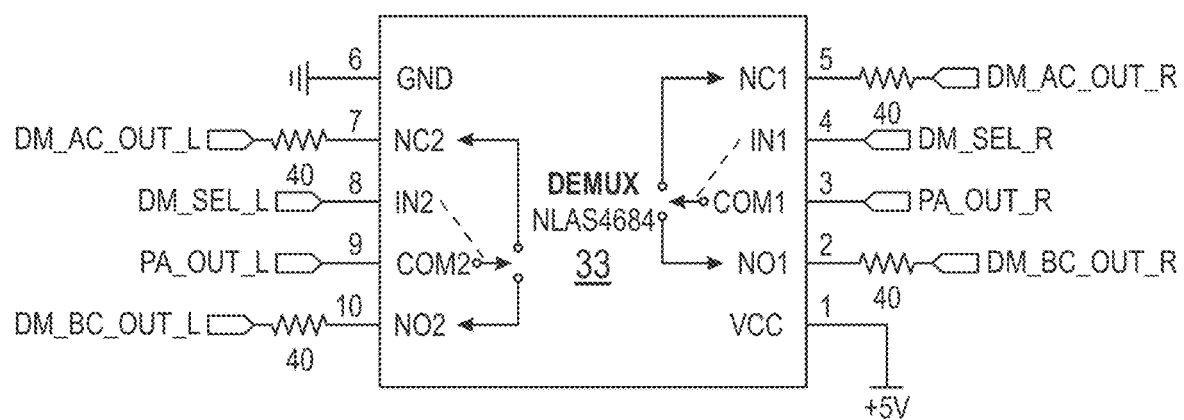
Figure 4B:
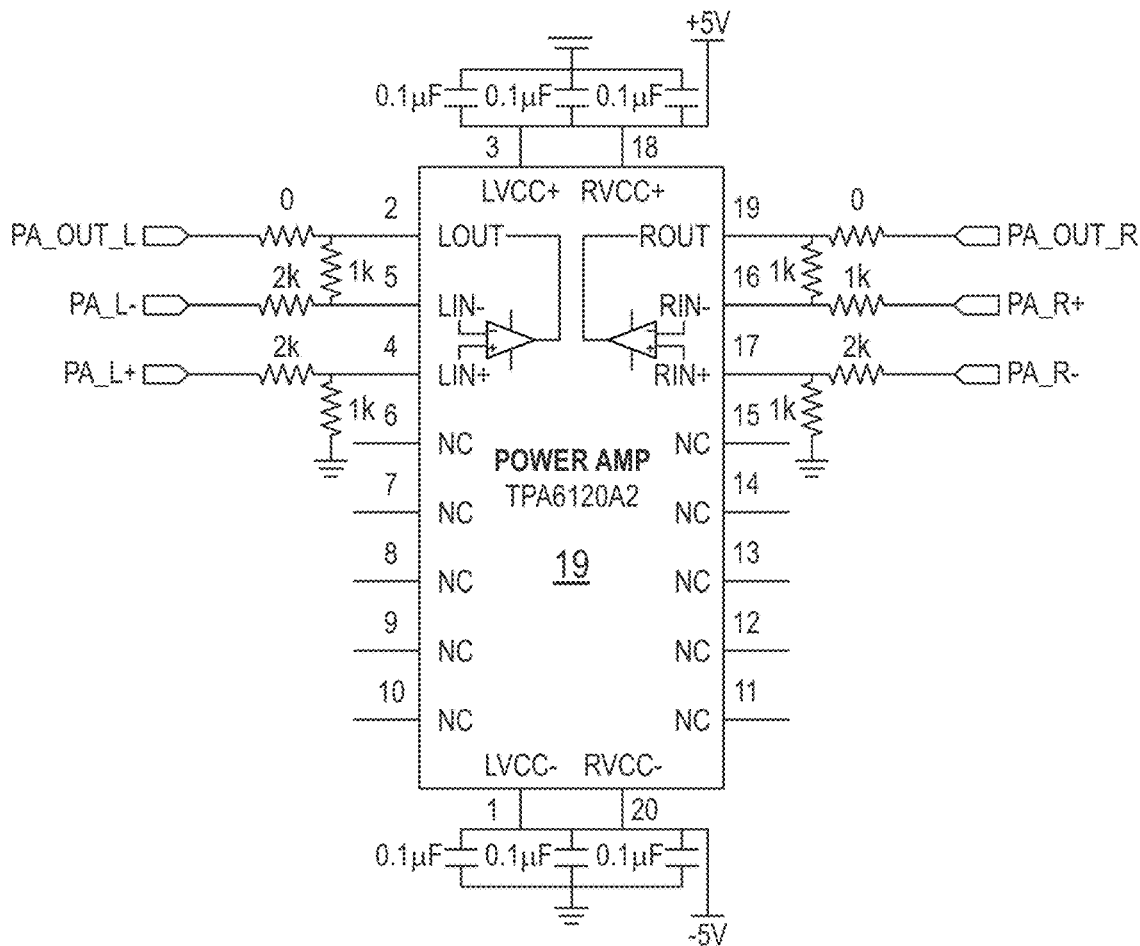
Figure 4B:
Figure 4B:
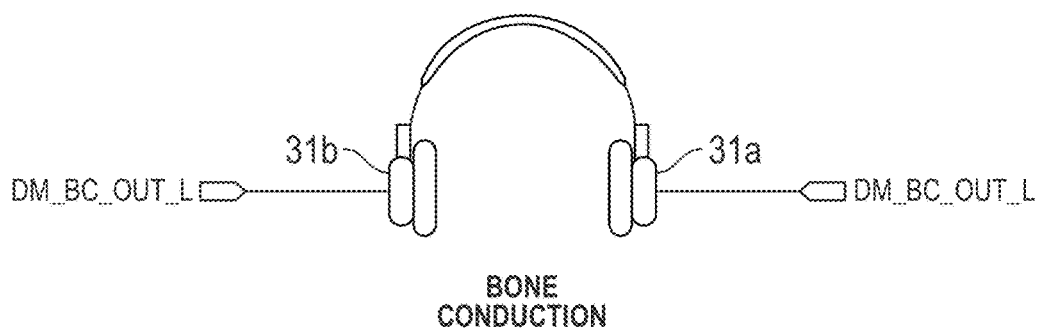

FIGS. 4A-4B are a second part of the circuit schematic (the first part being depicted in FIGS. 3A-3D). FIGS. 4A-4B show the component level integrated circuit 15 that implements the left and right channel pre-amplifiers 15a, 15b. It also shows the component level integrated circuit 19 that implements the left and right output amplifiers 19a and 19b.

The output transducers 21a, 21b shown in the block diagram of FIG. 2 comprise loudspeakers. However, they could instead comprise bone conduction transducers 31a, 31b as shown in FIGS. 4A-4B. In that case a demux chip 33 is provided to switch the output signal from the power amplifier 19 between the loudspeaker and bone conduction transducers as desired. The demux chip 33 is controlled by the FPGA via the DEMUX interface 32 on that chip.

Figure 5:
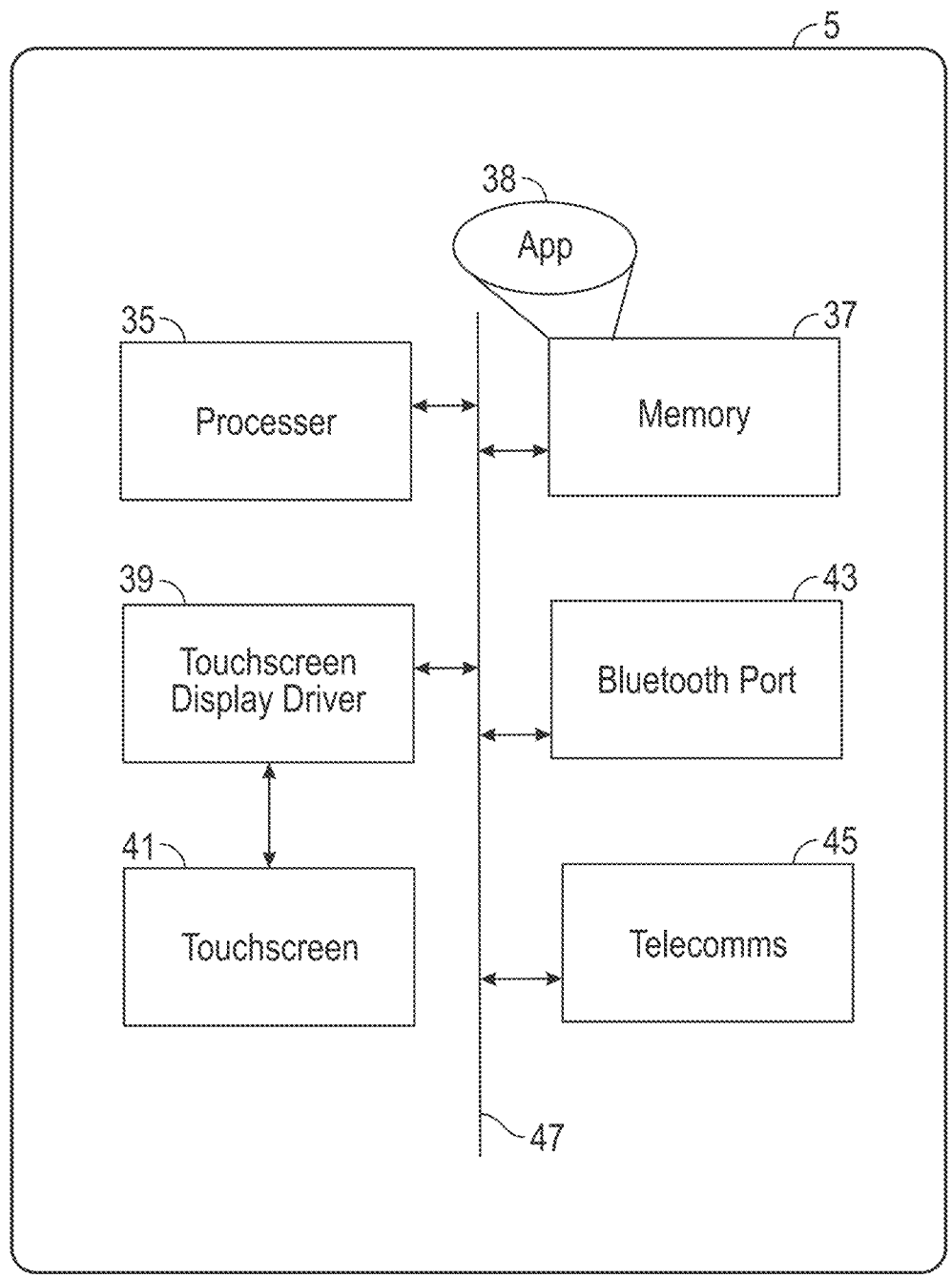
FIG. 5 is a high level block diagram of a user interface portion, in the form of a smartphone, of the sound delivery system.

Turning now to FIG. 5 there is depicted a block diagram of the smartphone 5. The smartphone 5 comprises a number of modules which are able to exchange data and commands via a data bus 47. The various modules comprise:
- a processor 35;
- an electronic memory 37;
- a communications module in the form of Bluetooth port 43 for communicating with corresponding Bluetooth port 9 of the transducer portion 7;
- a telecoms module 45 which allows the smartphone 5 to establish voice and data communications with a telecommunications network; and
- a touchscreen drive module 39, which drives touchscreen 41 and processes user data inputs received via the touchscreen and passes them to the processor 35.

It will be realised that the architecture shown in FIG. 5 is highly simplified and omits many components that are found in a smartphone. However, it will be sufficient for those skilled in the art to understand the preferred embodiment of the invention.

The memory 37 stores instructions that comprise a custom application, i.e. "App" 38 which the processor 35 executes in use in order to perform a method according to a preferred embodiment of an aspect of the present invention which will now be described. The programming of the App 38 is straightforward once the method, which will become apparent from the following discussion, is understood.

Referring again to FIG. 1, in use the user 3 dons the headphones 7 and switches the headphones and the smartphone 5 on so that Bluetooth communication is established there between.

Figure 7:
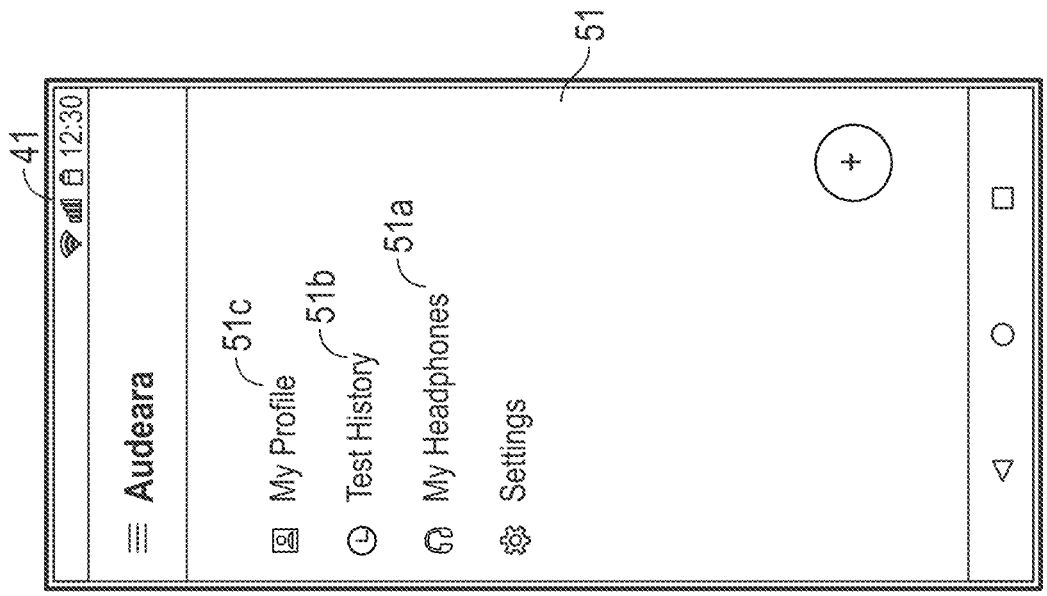
FIGS. 6 to 10 are screen shots of screens presented to a user by the smartphone.
Figure 6:
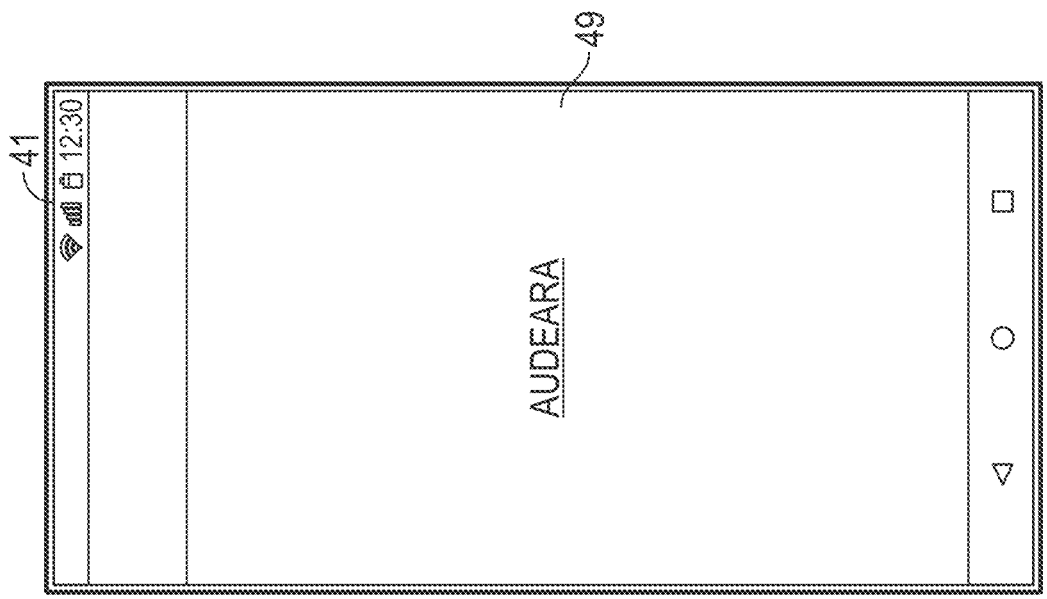

The user then operates the smartphone to initiate execution of the App 38, for example by clicking on an icon for the App, which displayed on touch screen 41. A splash screen 49 shown in FIG. 6 is then displayed to the user 3 and shortly thereafter a control menu screen 51 is displayed as shown in FIG. 7.

Figure 12:
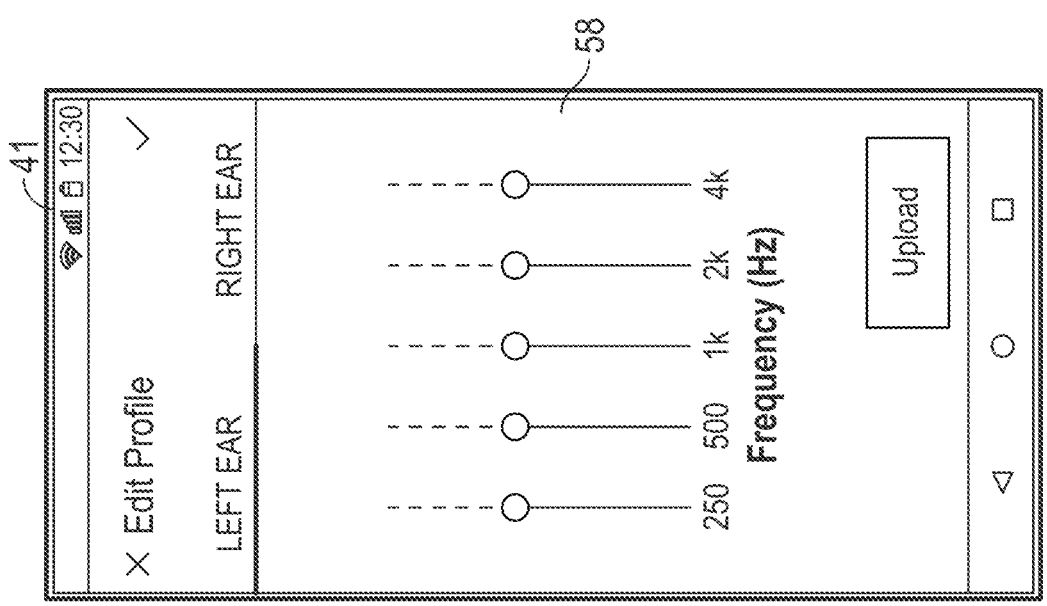

The control menu screen 51 presents the user 3 with three configuration options, 51a, 51b, 51c. The first option is "My Headphones" 51a. If the user has never used the App before and wants to quickly upload some equaliser style adjustments then he/she can choose the "My Headphones" option 51a. in response to that selection the processor 35 presents an equaliser screen 59 shown in FIG. 12. The App is programmed so that the user 3 can quickly set and upload equaliser preferences.

Alternatively if the user 3 has used the app 38 before and has pre saved hearing profiles then the user can choose a second option being "Test History" option 51b. In response to selecting the "Test History" option 51b the processor causes the display of a list view of previous models from which the user can select from and upload to the headphones 7 with or without an equaliser overlay.

Finally, if the user 3 is using the app 38 for the first time then the user can select the "My Profile" option 51c. Selecting the "My Profile" option 51c causes the processor to call up an audio modeling routine and set a personalised model to be uploaded with or without an equaliser overlay to the headphones 7. If an equalizer overlay is applied then the gain adjustment weights that have been determined based on the audiological testing are varied to take into account the user's equalization preferences. For example if the user prefers a bassier sound then the weights corresponding to lower frequency bands are increased.

Figure 9:
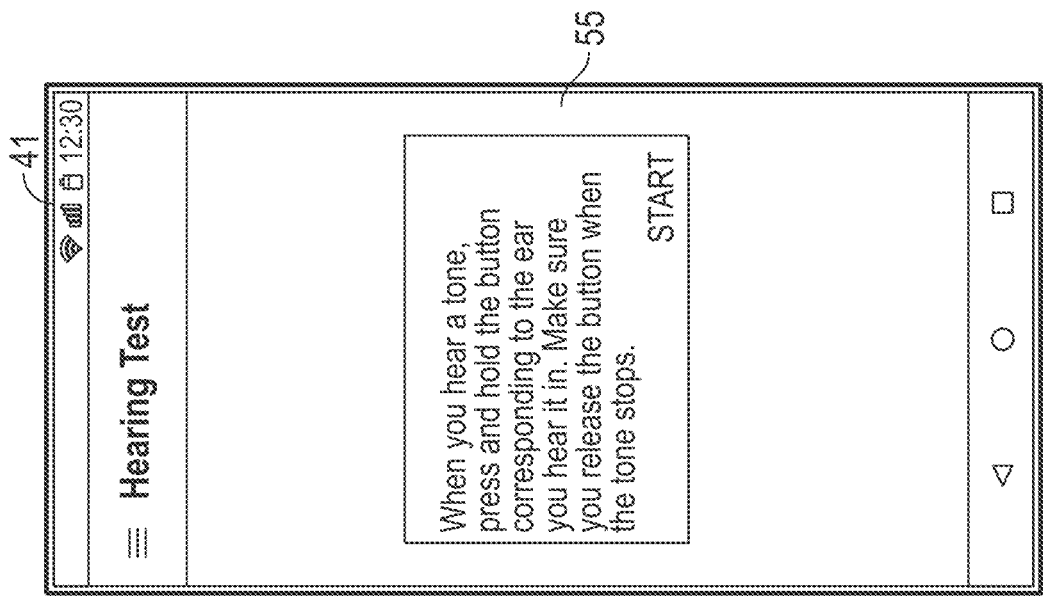
Figure 8:
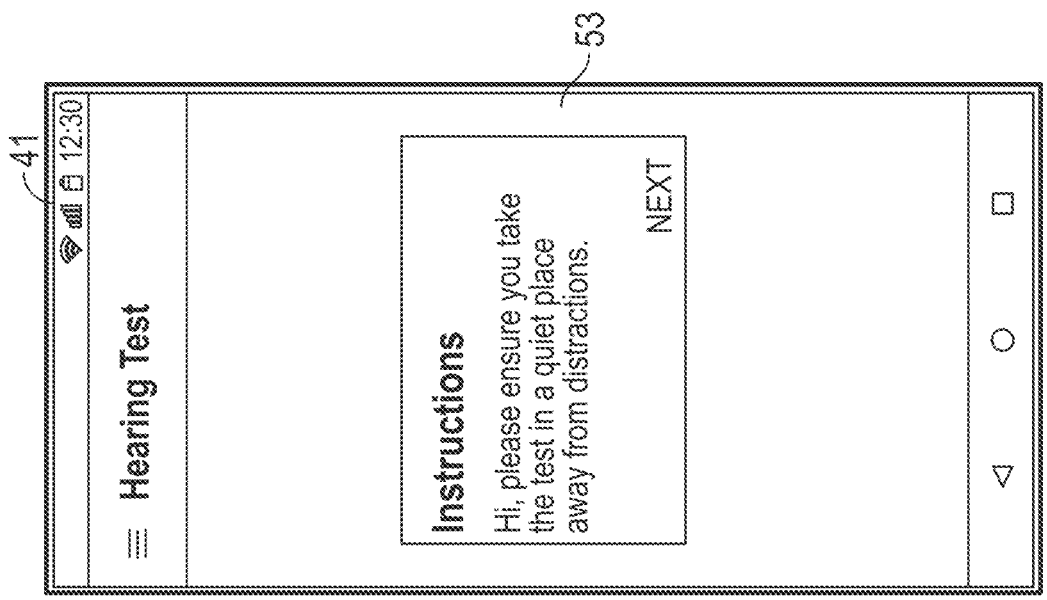
Figure 10:
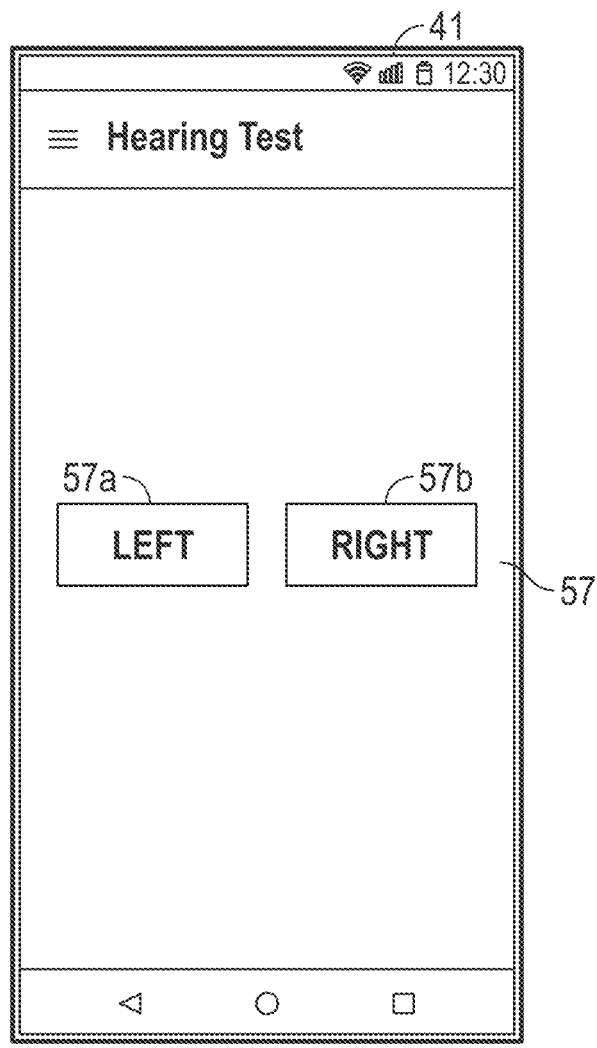

On selecting the "My Profile" option 51c the processor 43 causes screens to display prompting the user to help optimise the acoustic model as displayed in prompt screens 53 (FIG. 8) and 55 (FIG. 9).

Once the user 3 operates touch screen 41 to indicate that he/she is ready to undergo the audio model routine the app 43 displays the interface screen 57 and the user 43 is directed to respond to the software by pressing the "left" 57a or "right" 57b buttons. Upon doing so the processor communicates with the headphones 7 via the Bluetooth link to cause the loudspeakers in the headsets to present beeps in the user's left or right ear respectively.

Figure 11:
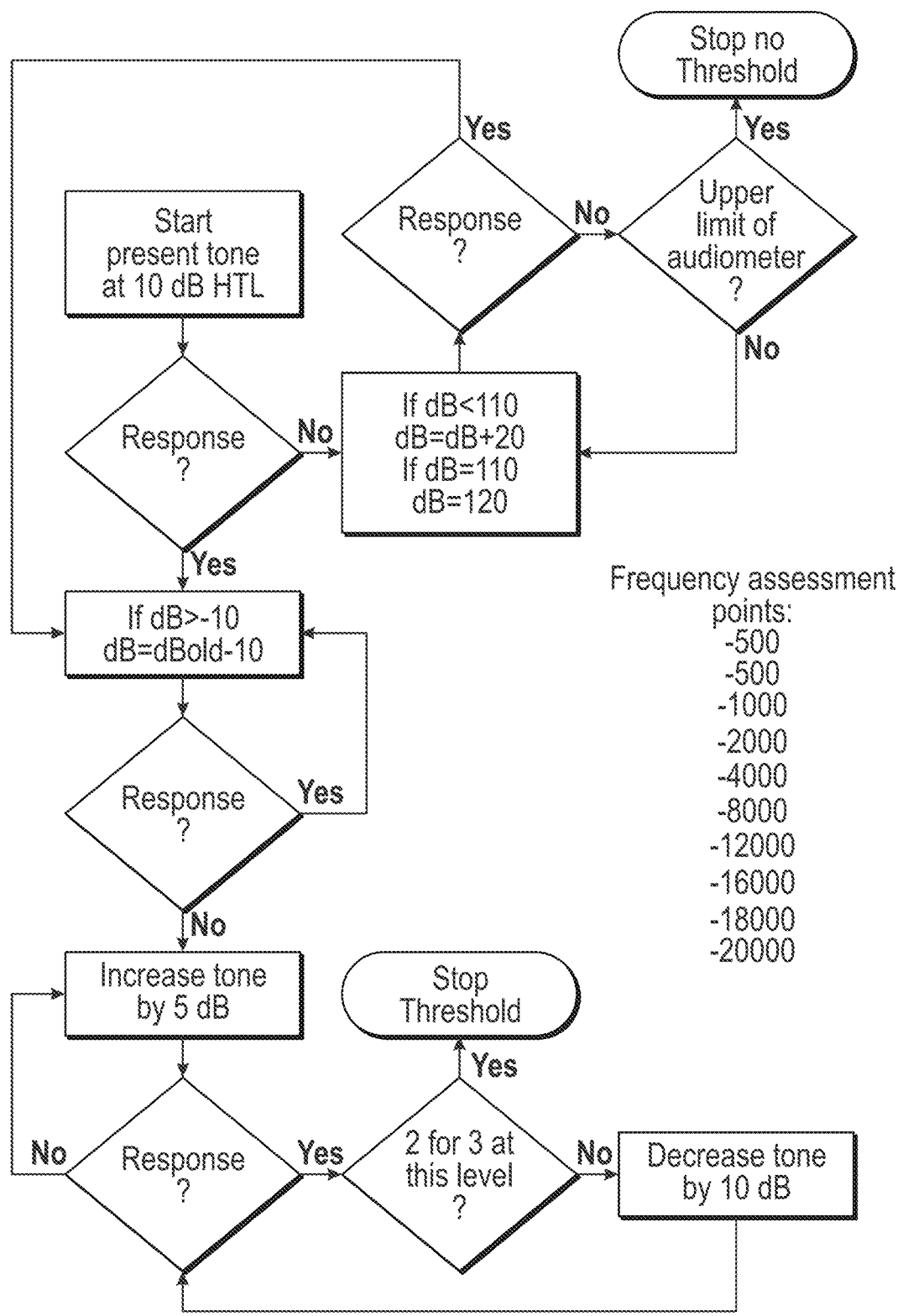
FIG. 11 is a block diagram illustrating a modeling method in accordance with an embodiment of the present invention.

The App then presents screens to step the user through a modeling method 59 that is shown in FIG. 11 and which is in accordance with a preferred embodiment of the invention. The modeling method 59 includes steps to identify the user's minimal perceived headset specific decibel threshold at each of a number of frequency assessment points. The determined specific decibel thresholds for the user are then saved into the audio model. The dB Threshold variable for each frequency is set in the boxes titled "Stop Threshold", in this step the assessment is stopped and the calculated dB value is saved. Alternatively, in the box "Stop No Threshold", the procedure is stopped and the correction dB is set to the maximum as the user has profound hearing loss at this frequency and has maximised the capabilities of the hardware. In the flowchart the box labelled "2 for 3 at this level?" comprises part of an error check loop. The user will actually be presented with that dB level three times before the program exits. If the user can hear it two out of three times then they are deemed to be able to hear it. The purpose of this is to avoid input error and the like. The audio model is a set of parameters for the user, including the decibel thresholds that are saved in the digital memory 37.

Figure 13:
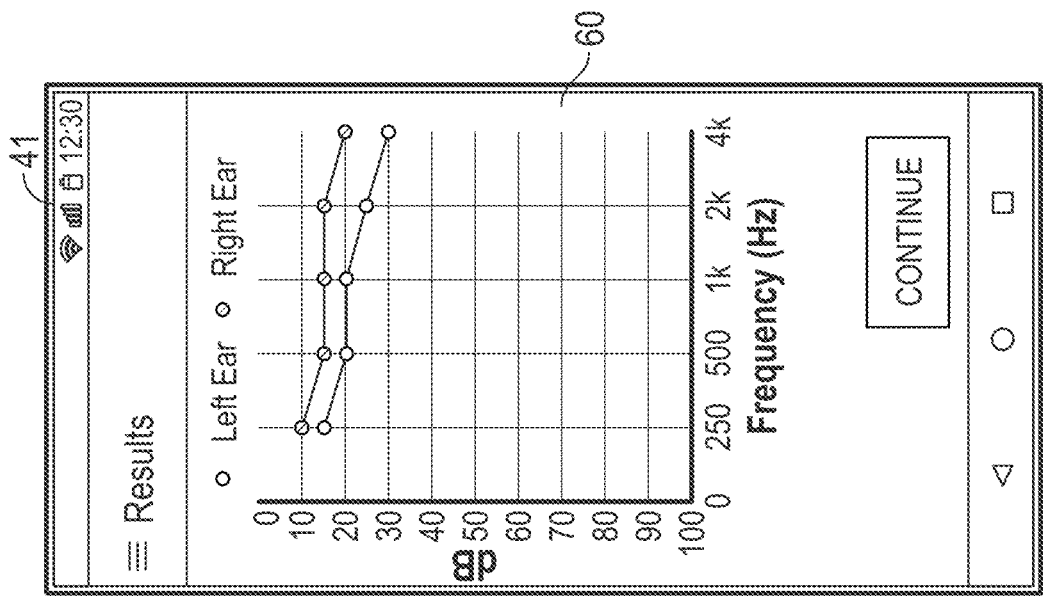
FIGS. 12 and 13 are screen shots of screens presented to a user by the smartphone.

On completion of the method 59 for each of the frequency assessment points, the App has successfully modelled the way in which the user perceives sound through the headset 7. The app 3 then converts the perceived model into a graphical depiction 60 as shown in FIG. 13 for review. The graph in FIG. 13 showing shows the user's left ear and right ear hearing response as assessed at each of a number of frequencies.

Figure 14:
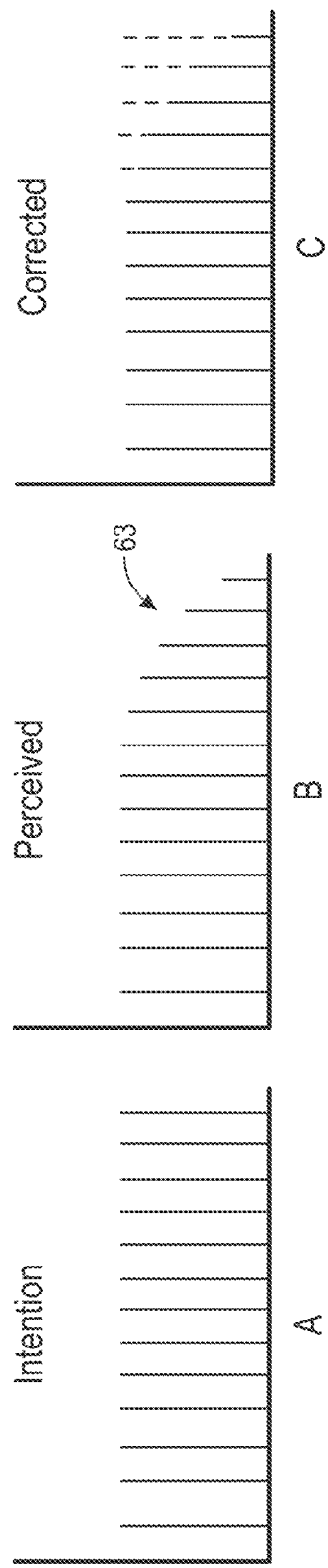
FIG. 14 comprises three frequency domain spectrograms. At left is the hearing response spectrogram of a person with normal hearing to a test audio signal. In the middle there is the hearing response spectrogram of a person with deteriorated hearing response in high frequency bands to the test audio signal. At right is the perceived audio response to the test signal subsequent to the test signal being gain adjusted to compensate for the high frequency loss.

With reference to frequency spectrum graphs of FIG. 14, the method 59 finds the user's perceived gain deficiency 63 in each specific frequency band in the audio spectrum. It then calculates weights (i.e. gain correction factors) by which future audio waveforms need to be gain adjusted in the frequency domain to correct the user's waveform back to perceived unity as intended. These weighting coefficients are then up loaded from the smartphone 5 into the headset FPGA 7. The FPGA then uses the uploaded weights in run time for the dynamic real time processing of uncompensated audio from the smartphone.

The App 43 then displays the equaliser screen 58 (FIG. 12) to the user 3. Here the user has the option to remain with a unity correction as per the audiological model or to use this base level correction with an equaliser overlay to allow the additional personalisation.

Once the user completes this customisation and selects "Upload", the model with or without the equaliser overlay as per the users preference are transitioned into frequency based coefficient corrections and are uploaded to the paired headset for configuration of the on-board signal processing corrections.

Figure 15:
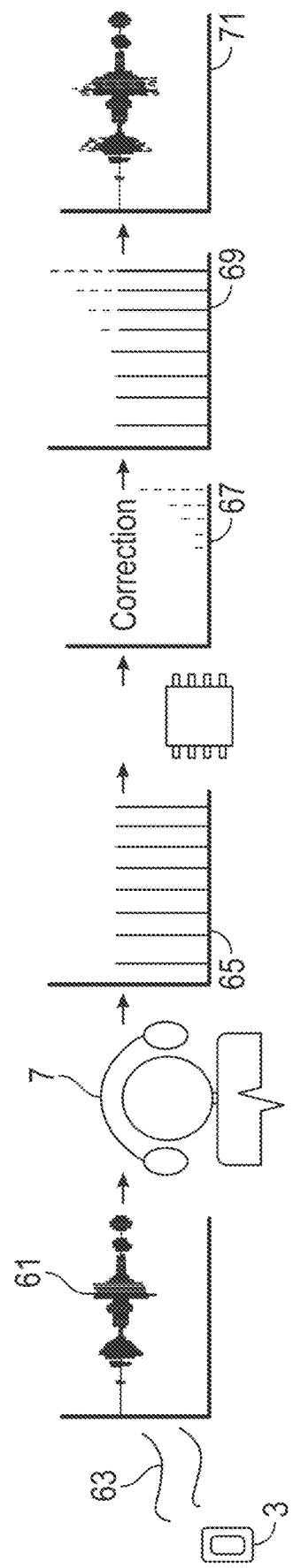
FIG. 15 is a flowchart of the steps performed by the sound delivery system delivery of audio to a user.

FIG. 15 is a flowchart showing how the FPGA is programmed to use the determined gain adjustment weights, i.e. the audiological model, to process a WAV file (or other audio file) to thereby apply the weightings produced in the audiological assessment with or without an equalizer overlay.

From left to right of FIG. 15, a digital audio signal 61 is transmitted to the headset 7 via a Bluetooth link 63. This received signal is transmitted into the on board FPGA (item 11 of FIG. 2) for signal processing. Inside the FPGA the time domain audio signal 61 is converted to the frequency domain 65 by the utilisation of an FFT this frequency domain signal is then gain adjusted against the patient's personal correction weightings 67 for each corresponding frequency bin to create a gain adjusted frequency domain representation of the signal. The FPGA 11 then undertakes an IFFT to render the signal in to a user specific time domain digital audio waveform 71. The digital audio waveform is then processed by the DAC (item 13 of FIG. 2) and analogue amplifiers and possibly noise cancellation modules to drive the transducers of the headphones.

It will therefore be understood that in a preferred embodiment of the invention a sound delivery system 1 (FIG. 1) is provided. The sound delivery system 1 includes at least one processing assembly which in the presently described embodiment includes the smartphone processor 35 and the headphone FPGA 11. A user interface is provided in the form of smartphone touchscreen 41 and touchscreen display driver unit 39. The touchscreen display driver unit 39 is coupled to the processor via a data bus 47. The sound delivery system 1 also includes at least one audio transducer. For example, either or both loudspeakers 21a, 21b (FIG. 4) and bone conduction transducers 31a, 31b (FIG. 4) are provided. The bone transducers are responsive to signals from the FPGA via suitable digital to analog converts and analog amplifiers.

The at least one processing assembly includes the processor 35 of smartphone 5. That processor is arranged, by virtue of it executing the instructions comprising app 38 that are stored in digital memory 37, to determine compensatory weights at each of a number of audio frequencies for the user. The processor determines the weights on the basis of user responses via the interface (e.g. touchscreen 41) to sounds delivered via the audio transducer (for example the loudspeakers of headset 7). The at least one processor also includes the FPGA 11 which is configured with the determined weights and which is therefore able to deliver audio signals to the user by modifying the audio signals in accordance with the determined weights.

In the presently described embodiment of the invention the user interface portion and the transducer portion of the sound delivery system are physically separate, though in data communication via a Bluetooth connection. It will be realized that in other embodiments of the invention the separation of the two units may not be so. For example, the headset could have a user interface, for example one or more buttons, mounted to the side which are coupled to an internal processor so that a user may initiate the automatic audiological assessment and then press one or other of the buttons to indicate a hearing threshold for a presented audio signal. Such an arrangement would not require a separation of the user interface portion and the transducer (i.e. headset) portion. In such an embodiment the processing assembly might comprise a single, suitably programmed, high frequency processor that is capable of both running the audiological assessment method and also performing the FFT and IFFT functions with gain adjustment according to the determined weights for the user.

Figure 16:
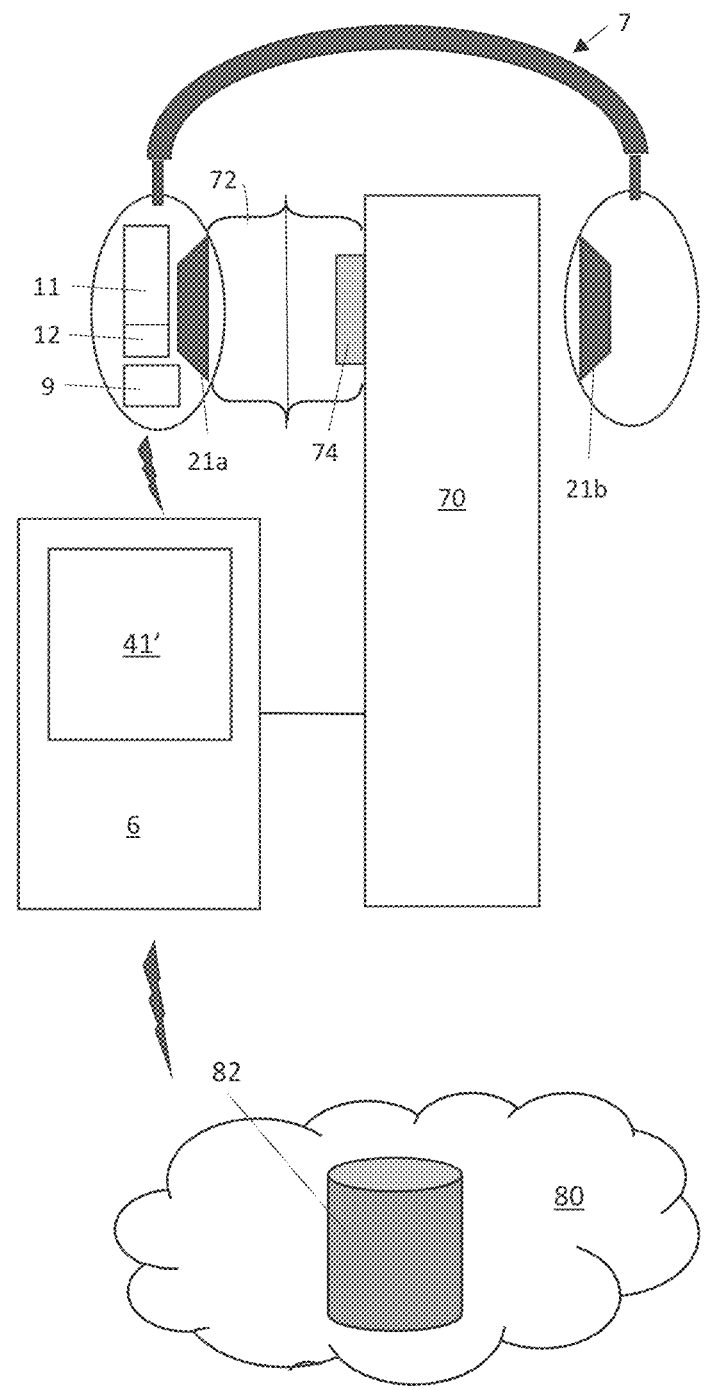
FIG. 16 is a schematic diagram showing the equipment employed in a calibration method of another aspect of the present invention.

Turning to FIG. 16 there is shown a schematic diagram of an embodiment of calibration equipment employed for the factory calibration of a sound delivery system, here in the form of the customisable sound delivery system (or "SDS") 1, as described above. The SDS of the present embodiment includes a set of headphones 7 having a pair of audio transducers 21 and a remote computational device, here in the form of a laptop computer or tablet 6. Note that the laptop computer or tablet has many components—for example touch screen 41'—in common, at least functionally, with the smartphone 5, described hereinabove. The headphones include a processor 11 and associated memory 12 that communicates with remote devices, such as laptop computer 6, via a communications module 9. The laptop computer 6 may also communicate with remote storage, such as database 82 held in a remote storage facility—sometimes referred to a "cloud storage"—accessible via a network (not shown), whether public or virtual private network.

The equipment necessary for calibration of an individual headset 7, includes a reference SPL meter 70 which is attached to a selected acoustic transducer, here left speaker 21a, by an acoustic coupler 72 in order to exclude external noise during calibration testing. Suitable reference SPL meters include the DigiTech QM1592 Pro Sound Level Meter supplied by Jaycar Electronics of Australia or, particularly for headphone sets, the bilateral EARS stand supplied by miniDSP of Hong Kong (see www.minidsp.com). It will be appreciated that it is not always economically viable to calibrate every headset produced. Instead, headsets of a particular design or "model" may be manufactured to quality standards of, for example +/−2 dB A, and a representative headset from a given production run subject to the calibration procedures described in relation to the present embodiment. By way of example, should the transducer pair be re-specified or redesigned, a fresh calibration would be conducted for the model variant. It will be appreciated that, in other embodiments for some particular medical applications, it may be desirable to calibrate each and every headset individually to achieve higher accuracy.

Figure 18:
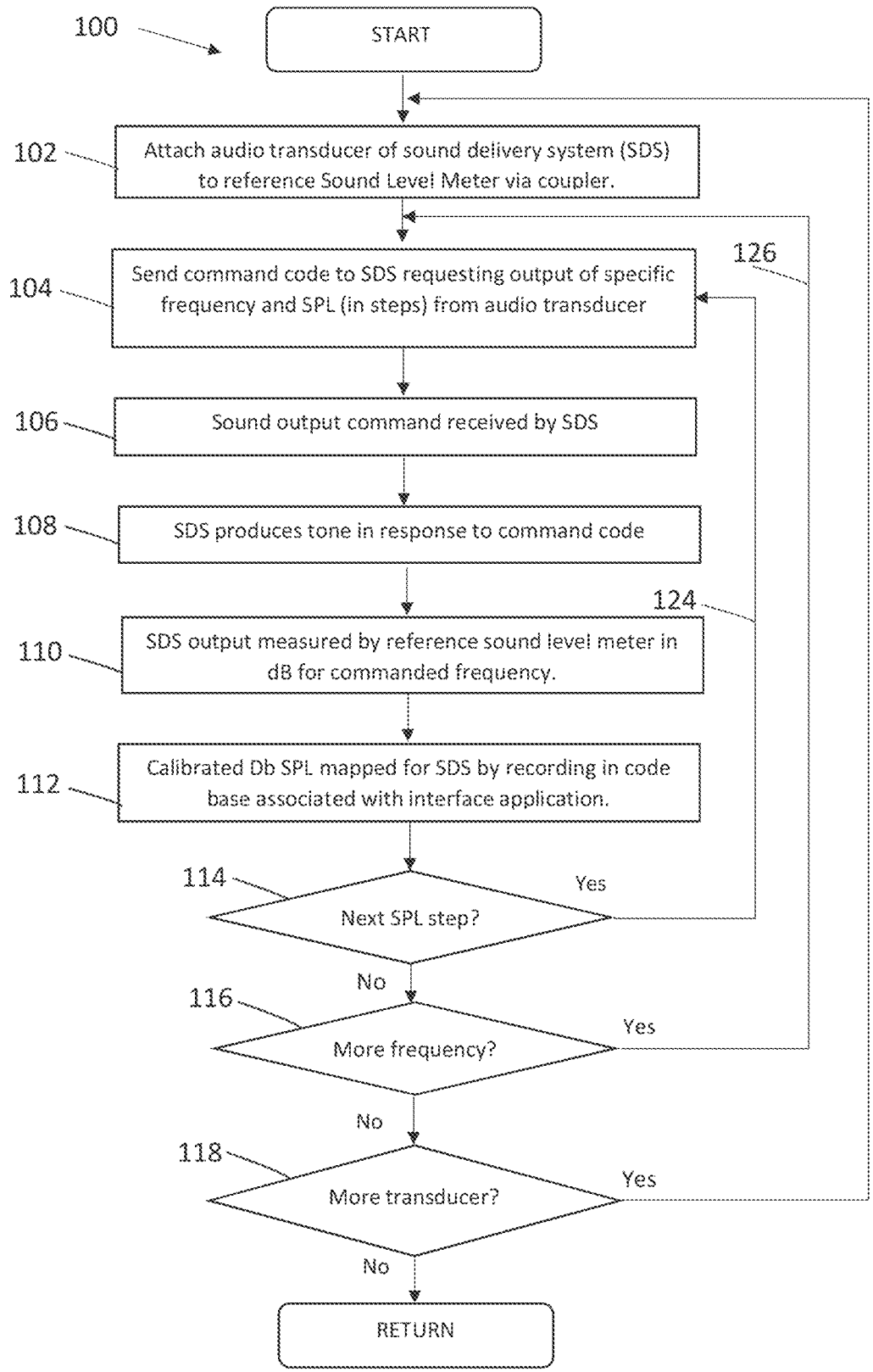
FIG. 18 is a flowchart of steps in a method for carrying out the calibration method employing the components illustrated in FIG. 16 to produce the results tabulated in FIG. 17.

FIG. 18 is a top level flow diagram of the sequence of steps in an embodiment of the calibration method 100 of the second aspect of the invention, here employing the equipment and optional infrastructure illustrated in FIG. 16. In step 102, the headphone body or headset 7 of a representative SDS containing a first audio transducer in the form of speaker 21a is coupled by to the reference sound pressure meter 70 by acoustic coupler 72, directing produced sounds to a microphone 74 of the SPL meter. The first of a sequence of command codes, targeted at speaker 21a, are then sent to the headphone assembly 7 in step 104 requesting output of a discrete test tone of specific frequency and sound pressure level, for example a command code requesting 100 Hz at 0 dB. In step 106 the command code is acknowledged by the communications interface 9 of the headphone assembly 7. In step 108, the processor 11 operates in response to the command code to cause the speaker 21a to reproduce a test tone, which in turn is measured by the reference sound level meter 70 in step 110.

In step 112 the SPL reading obtained by the reference SPL meter 70 is recorded for transfer to a database associated with a user interface application for the SDS 1. Desirably, a mapping of command codes input to the processor 11 and SPL readings obtained from a transducer 21 via the microphone 74 of reference SPL meter 70 is built up to produce a mapping table in the database. The SPL mapping resulting from the calibration may be stored, at least temporarily, in a database held locally in the local memory 12 associated with processor 11, in memory of the handheld device 6 controlling calibration, or most desirably and eventually in a remote database 82 held in a cloud storage facility 80. The remote database 82 suitably also contains an interface application for selective down-loading to any compatible user interface device, and incorporates the SPL mapping for the particular model and/or production run of the headset 7 that has undergone calibration. This effectively provides a single point of calibration, thus obviating the need for "paired" interface devices and transducer hardware which typically adds to costs and/or inconvenience to achieve a similar level of accuracy.

In step 114, control is passed back to step 104 where after a delay of 0.5 s the command code for a subsequent test tone having the same frequency but a different SPL level, for example 10 dB, is produced in step 104. Return loop 124 is then repeated through each of the desired SPL levels (for example in 10 dB steps to 100 dB).

At the conclusion of the desired SPL level range, control drops through from the Next SPL in decision box 114 to decision box 116 wherein a subsequent frequency step is selected, for example 250 Hz recommencing at an SPL level of 0 dB. Control then passes back to loop 124 and the 250 Hz in stepped through each of the desired SPL levels.

At the conclusion of each of the desired frequencies represented by loop 126 (and SPL levels within each frequency), for example 500 Hz, 1 kHz, 2 kHz, 4 kHz, 8 kHz and 16 kHz, control drops to decision box 118 wherein a user will be prompted to move (if required) or switch (in the case of a bilateral meter) the acoustic coupler and reference SPL meter 70 to the other of the acoustic transducers, e.g. speaker 21b, in step 102. Subsequently control returns to step 104 to repeat the test tone process for the other transducer at each selected frequency and SPL level.

In use, by way of example, if the command code "025-50" issued by an interface device 6 requiring an SPL of 50 dB at 1 kHz was reproduced as a test tone of 45 dB by the left transducer 21a, the mapping associated with the interface application appropriate to the headset model would make the appropriate adjustment during 1 kHz tone production by processor 11. See the example results table depicted in FIG. 17 wherein the mapping may be derived from the difference or offset between the requested and measured SPL results for the left transducer 21a. It will be appreciated that there will be a similar table portion generated for the right transducer 21b, across the full range of desired frequencies and SPLs.

In compliance with the statute, the invention has been described in language more or less specific to structural features or methodical steps. The term "comprises" and its variations, such as "comprising" and "comprised of" is used throughout in an inclusive sense and not to the exclusion of any additional features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

Throughout the specification and claims (if present), unless the context requires otherwise, the term "substantially" or "about" will be understood to not be limited to the value for the range qualified by the terms.

Any embodiment of the invention is meant to be illustrative only and is not meant to be limiting to the invention. Therefore, it should be appreciated that various other changes and modifications can be made to any embodiment described without departing from the spirit and scope of the invention.

We claim:

1. A sound delivery system comprising:
   a processing assembly including at least one processor and an electronic memory;
   an interface for a user coupled to the at least one processing assembly;
   at least one audio transducer responsive to the processing assembly for delivering sound to the user; and
   wherein the electronic memory is accessible by the at least one processor and stores:
      instructions for the processor to determine compensatory weights at each of a number of audio frequencies for the user on the basis of user responses via the interface to sounds delivered via the audio transducer and to deliver audio signals to the user modified in accordance with the determined weights via said audio transducer;
      a code base utilised by an audio application interface of the sound delivery system;
      wherein the sounds delivered via the transducer for determining the compensatory weights are generated by a transducer processor mounted within a transducer portion which includes the at least one audio transducer; and
   wherein the sound delivery system is calibrated in accordance with a method of calibrating the sound delivery system, the method including:
      transmitting from a remote user interface device for an audiological testing apparatus, a sequence of command codes for specifying predetermined characteristics of test sounds;
      receiving the command code sequence at a communications assembly of the audiological testing apparatus;
      providing the command code sequence to the processing assembly of the audiological testing apparatus;
      reproducing by a selected at least one audio transducer, predetermined test sounds under control of said at least one processor according to the command code sequence;
      measuring with a reference meter proximate to the audio transducer, characteristics of test sounds reproduced by the audiological testing apparatus;
      comparing the measured characteristics of the reproduced sounds with the predetermined characteristics of the test sounds;
      producing a mapping of specified test sounds to sounds reproduced by said at least one audio transducer; and
      storing the mapping in an electronic memory associated with the processing assembly.

2. The sound delivery system of claim 1 wherein a processor of the processing assembly is mounted with said at least one audio transducer.

3. The sound delivery system of claim 2 wherein the audio transducers comprise a pair of speakers mounted in a set of headphones.

4. An automatic audiological testing apparatus comprising:
   a processing assembly having at least one processor;
   an electronic memory in communication with the processor and containing instructions for execution by said at least one processor;
   a user interface in communication with the processor; and
   at least one audio transducer mounted with the processing assembly and responsive to the at least one processor for delivering sound to a user;
   wherein the electronic memory stores instructions for the processor to determine compensatory weights at each of a number of audio frequencies for the user on the basis of user responses via the interface to sounds at a number of different frequencies;
   wherein the sounds delivered via the transducer for determining the compensatory weights are generated by a transducer processor mounted within a transducer portion which includes the at least one audio transducer; and
   wherein the audiological testing apparatus is calibrated in accordance with a method of calibrating the audiological testing apparatus, the method including:
   transmitting from a remote user interface device for an audiological testing apparatus, a sequence of command codes for specifying predetermined characteristics of test sounds;
   receiving the command code sequence at a communications assembly of the audiological testing apparatus;
   providing the command code sequence to the processing assembly of the audiological testing apparatus;
   reproducing by a selected at least one audio transducer, predetermined test sounds under control of said at least one processor according to the command code sequence;
   measuring with a reference meter proximate to the audio transducer, characteristics of test sounds reproduced by the audiological testing apparatus;

comparing the measured characteristics of the reproduced sounds with the predetermined characteristics of the test sounds;

producing a mapping of specified test sounds to sounds reproduced by said at least one audio transducer; and storing the mapping in an electronic memory associated with the processing assembly.

5. The sound delivery system of claim 1 wherein the transmitting step involves use of wireless transmission employing a local or near field communications standard.

6. The sound delivery system of claim 1 wherein the test sounds include a sequence of discrete sounds of different frequencies and different sound pressure levels (SPL) within each frequency, suitably covering a typical range of human hearing.

7. The sound delivery system of claim 6 wherein the frequencies of the test sounds are in a range of frequencies from 10 Hz to 30 kHz, suitably 20 Hz to 20 kHz.

8. The sound delivery system of claim 6 wherein the sound pressure levels of the test sounds are in a range from −10 dB to 120 dB, suitably 0 dB to 110 dB, within each discrete sound frequency.

9. The sound delivery system of claim 6 wherein each of the discrete test sounds in the sequence is of equal duration and spaced apart from adjacent sounds by a period of silence.

10. The sound delivery system of claim 9 wherein the discrete sound duration is in a range from 0.1 milliseconds to 5 seconds, suitably 100 milliseconds to 1 second.

11. The sound delivery system of claim 9 wherein the silence period in a range from 0.1 milliseconds to 5 seconds, suitably 100 milliseconds to 1 second.

12. The sound delivery system of claim 1 wherein the storing step involves storing the test sound mapping in the code base utilised by the audio application interface of the sound delivery system.

13. The sound delivery system of claim 12 wherein the code base is stored in a non-volatile portion of the electronic memory.

14. The sound delivery system of claim 12 wherein the sound delivery system further comprises an interface application, wherein the code base is also stored remotely in a database and associated with the interface application for the sound delivery system, for down-loading with the interface application on request.

* * * * *